United States Patent [19]

Hodge

[11] 4,452,052
[45] Jun. 5, 1984

[54] PERFUMING MEANS FOR JEWELRY

[76] Inventor: Margaret Hodge, 27 E. 65th St., New York, N.Y. 10021

[21] Appl. No.: 310,031

[22] Filed: Oct. 9, 1981

[51] Int. Cl.³ ............................................. A44C 13/00
[52] U.S. Cl. .......................................... 63/1 R; 63/2; 63/DIG. 2
[58] Field of Search ................. 63/1, DIG. 2; 239/36, 239/57, 58, 59, 60

[56] References Cited

U.S. PATENT DOCUMENTS

| | | |
|---|---|---|
| 168,972 | 10/1875 | Dayton . |
| 331,937 | 12/1885 | Birge . |
| 1,267,067 | 5/1918 | Flagg . |
| 1,625,375 | 4/1927 | Reyes . |
| 1,931,132 | 10/1933 | Hinckley ............................ 239/57 |
| 2,058,274 | 10/1936 | Vivaudou . |
| 2,550,828 | 5/1951 | Lawson . |
| 2,740,662 | 4/1956 | Scott . |
| 3,888,416 | 6/1975 | Lin ................................... 239/60 |
| 3,946,945 | 3/1976 | Odioso et al. ................ 239/60 X |
| 4,056,951 | 11/1977 | Black . |
| 4,301,949 | 11/1981 | Palson et al. ................. 239/59 X |

FOREIGN PATENT DOCUMENTS

| | | |
|---|---|---|
| 1180181 | 10/1964 | Fed. Rep. of Germany . |
| 2409955 | 9/1975 | Fed. Rep. of Germany . |
| 2220207 | 3/1973 | France ............................ 63/DIG. 2 |
| 560143 | 3/1975 | Switzerland ....................... 239/59 |
| 599124 | 3/1948 | United Kingdom . |

Primary Examiner—Robert A. Hafer
Assistant Examiner—Perry Knutson
Attorney, Agent, or Firm—Darby & Darby

[57] ABSTRACT

An earring structure is disclosed having an interior compartment which houses a removable perfume cartridge. The perfume cartridge comprises a cartridge base containing perfumed material, and a rotatable top piece having an aperture through which fragrance may escape from the perfumed material to the ambient. Rotation of the top piece relative to the cartridge base changes the aperture area which is exposed to the perfumed material, thus permitting the wearer to block the escape of fragrance when desired and providing an adjustable range of fragrance strengths.

8 Claims, 5 Drawing Figures

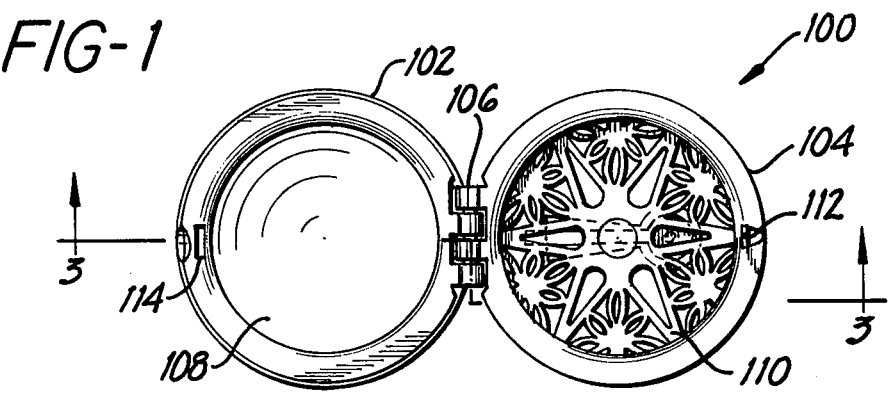
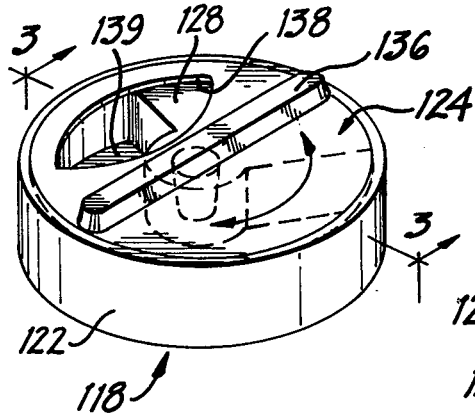
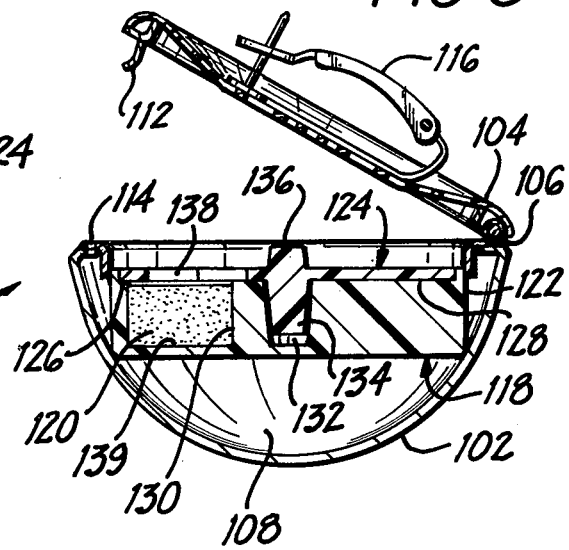
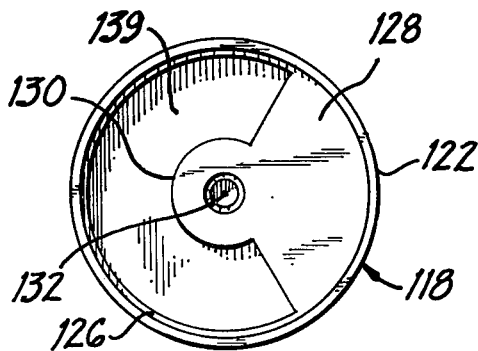
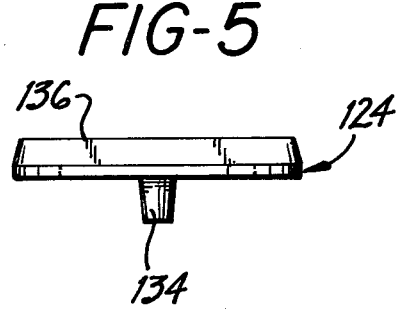

PERFUMING MEANS FOR JEWELRY

BACKGROUND OF THE INVENTION

This invention pertains to the field of personally worn ornamental jewelry, and particularly to such jewelry which is designed to hold a quantity of perfumed material.

The use of essential oils and similar perfumed material in earrings, lockets and other items of personal jewelry is well known in the art. The advantages of such perfumed ornaments are obvious, as they permit the wearer to position a source of fragrance at provocative bodily locations without the need to constantly reapply the perfumed material as it evaporates. However, due to numerous deficiencies in existing designs, this arrangement has not achieved a level of public acceptance sufficient to bring it out of the category of a novelty item.

Presently available perfume carrying ornaments include earrings containing a wad of cotton which may be saturated with perfume by the user. The fragrance then escapes from the perfume saturated cotton to the ambient atmosphere through a perforated backing or similar gas permeable material. The disadvantage to this system is that the wearer is regularly fumbling with bottles of alcohol based perfume, frequently spilling it on the varnished wooden tops of dressing tables and thus marring the finish of the wood. If the user overcomes this obstacle, he or she invariably ends up with perfume saturated fingers which must be rinsed off, thus wasting precious time and costly perfume. More recently, pellets of solid wax-based perfuming agents have been proposed as a means of solving the problems created by saturated cotton swabs. However, these pellets must still be directly handled by the user, and are generally awkward to insert as they become very slippery as soon as exposed to the heat of the user's fingertips.

Another factor which has discouraged widespread acceptance of perfumed jewelry has been the fact that it is not well suited for use with expensive, high quality perfumes. Presently available designs provide a continuous outpouring of fragrance from the moment the perfume is inserted until all of it has evaporated. Since it would be senseless to apply a fresh charge of costly perfume hours before its intended use, the wearer would have to carry such perfume in a separate container so that the perfume could be added to the ornament at the appropriate time. In addition, the user cannot charge the ornament with more perfume than will be needed for one wearing, as the excess could not be stored for later use. This defeats the most useful aspect of perfumed jewelry, which is to provide a source of fragrance on one's person that need not be constantly replenished from an external source.

A further hindrance to the popularity of perfumed jewelry has been the inability of such jewelry to accommodate widely varying strengths of fragrance as well as differences in personal preference for providing a desired fragrance strength. Since the prior art designs do not contain any means for adjusting the rate at which a fragrance escapes from the perfumed material, the user cannot compensate for unusually strong or delicate fragrances. These ornaments are thus severely limited in their application, due to the wide range of personal preferences for a desired level of fragrance strength.

It is therefore an object of this invention to provide an easily refillable perfumed jewelry ornament in which the user may insert a fresh charge of fragrance without physically contacting the perfumed material.

It is another object of this invention to provide a perfumed jewelry ornament which can repeatedly store perfume until ready for use and then readily be converted to emit the fragrance therein.

It is a further object of this invention to provide a means for adjusting the relative level of fragrance strength which is emitted from an article of jewelry.

It is yet another object of this invention to provide the above objects in a compact, economical and easy to use structure.

It is feature of this invention that perfume is permanently stored in a discreet disposable cartridge adapted for placement in an article of jewelry.

It is another feature of the invention that the escape of fragrance from an article of jewelry can be turned on or off to conserve the perfumed material therein.

It is a further feature of this invention that the rate of escape of a fragrance from perfumed material in an article of jewelry can be adjusted to provide a range of fragrance strengths suitable to the chosen perfume and to the wearer's taste.

BRIEF DESCRIPTION OF THE DRAWINGS

FIG. 1 is a plan view of an earring structure in accordance with the present invention;

FIG. 2 is a perspective view of a perfume cartridge adapted for insertion in the earring structure of FIG. 1;

FIG. 3 is a cross-sectional view of the earring structure of FIG. 1 with the perfume cartridge inserted therein, taken along section lines 5—5 of FIGS. 1 and 2.

FIG. 4 is a plan view of the earring cartridge of FIG. 2, taken along its cylindrical axis, with its top piece removed to show the interior of the cartridge; and FIG. 5 is an elevational view of the top piece of the perfume cartridge of FIG. 2.

DESCRIPTION OF THE PREFERRED EMBODIMENT

Referring now to FIGS. 1, 2 and 3, there is shown an illustrative apparatus, which embodies the objects and features of the present invention. An ornamental casing is provided in the form of an earring structure 100, comprising a decorative dome-shaped facing 102 and a backplate 104 which is movable into and out of closed relation with the facing 102.

As seen in FIG. 1, facing 102 and backplate 104 are connected by a hinge 106 or other suitable connector which permits the backplate 104 to be swung away from the facing 102, exposing the interior compartment 108 therein. The embodiment shown uses a filigreed backing 110 to permit the escape of fragrance contained in the compartment 108 to the ambient atmosphere. Cooperative fastening means such as tab 112 and receiving notch 114 are provided to firmly hold the facing 102 and backplate 104 in closed relation when the earring structure 100 is in use. A spring loaded clamp and post 116, or any of various other fastening arrangements well known in the art, are attached to backplate 104 as seen in FIG. 3, to provide attachment of the earring structure 100 to the wearer's earlobe.

FIGS. 2 and 3 illustrate a perfume cartridge 118, which is specially adapted for storing a perfumed material 120 and dispensing its fragrance into the atmosphere at varying rates of escape. The cartridge 118 is a two-piece unit comprising a cylindrical one piece container or base 122 as seen in FIGS. 2 and 4 and a substantially disc-shaped top piece 124 as seen in FIGS. 2, 3 and 5. The cartridge may be formed of any suitable material which is impervious to the fragrance of the perfumed material to be contained, as is well known in the art. Base 122 is formed with an inner ridge 126 disposed about the periphery of a c-shaped depression 139 and co-planar with the top surface of a plateau section 128 to provide continuous support for the periphery of disc-shaped top piece 124 which is mounted thereon, as seen in FIGS. 3 and 4. FIG. 4 also shows the preferred circular arrangement of the interior of base 122, formed by C-shaped depression 139 abutting the substantially pie-segment shaped plateau section 128. In the center of base 122 is a substantially columnar projection 130 with a tapered cavity 132 extending down the center of the column. When the top piece 124 is joined with base 122, tapered cavity 132 houses a correspondingly tapered boss 134 which is integral with top piece 124 and defines its axis of rotation. A raised bar 136 is diametrically disposed across the upper surface of the top piece 124 to aid in the rotation of the top piece relative to the base 122 of cartridge 118. This rotation of top piece 124 changes the overlapping relationship of aperture 138 and plateau section 128, thereby effectively changing the aperture's size with respect to the perfumed material 120 located in depression 139.

In a preferred embodiment of the invention, perfumed material 120 comprises a wax-based material which is solid at room temperature. It is loaded in cartridge 118 by heating the material until it becomes liquid, pouring this molten liquid into depression 139 in the base 122 of the cartridge, and allowing the material to solidify. Top piece 124 is then mounted on base 122, thereby encasing the perfumed material 120 in the cartridge 118, eliminating the possibility of spillage. As the material evaporates and exits the cartridge 118 through aperture 138, depression 139 gradually empties, but the unevaporated perfumed material 120 remains affixed to the walls of depression 139. While the invention may be practiced in other forms, the use of a removable cartridge with solid perfume encased therein provides both a convenient device for interchanging various fragrances in the same article of jewelry and a highly effective marketing package in which to sell perfume.

In operation, the wearer opens the backplate 104 of the earring structure 100 and mounts or inserts a perfume cartridge having a desired fragrance in compartment 108. If the user does not immediately want to use the perfume, the setting of aperture 138 is maintained in the closed position, with the aperture 138 located directly over plateau section 128 to block the escape of fragrance from cartridge 118. The wearer then closes the backplate 104, snaps together fastening means 112 and 114, and attaches the earring to an earlobe for decorative display. When an occasion arises for using the perfume 120, as at the end of a business day, the wearer removes the earring structure 100, opens backplate 104 and rotates top piece 124 via raised bar 136 to move the aperture 138 wholly or partially over depression 139 containing perfumed material 120. As seen in FIG. 2, the aperture setting may be chosen so that part of the aperture 138 is over plateau section 128 and the rest of the aperture is over depression 139. By changing the aperture setting to cover more or less of the plateau section 128, the wearer may adjust the rate at which fragrance escapes from perfumed material 120 in the cartridge, thus providing a wide range of fragrance strengths to compensate for the strength of the perfume being used and to suit the wearer's individual taste. The tapered fit of boss 134 and cavity 132 provides a frictional interface between top piece 124 and base 122 which prevents the selected aperture setting from changing when the earring is in place. After making the desired setting of aperture 138, the wearer closes backplate 104, attaches the earring to the earlobe as before, and then forgets about fragrance for the rest of the evening, leaving time for more important affairs. At nights end the wearer removes the earring, opens the backplate and resets the aperture 138 over plateau section 128 to again block the escape of fragrance and thus preserve the remaining perfumed material 120 left in cartridge 118.

It should be noted that cartridge 118 may be changed several times during the course of a day to achieve a variety of different fragrances suited to the moods and occasions of the day, or may be stored in the earring indefinitely and only used when desired. The advantage of the cartridge arrangement in the first case lies in the provision of compact, independent storage units for various fragrances which may be carried in a handbag or pocket and interchanged in an earring or like jewelry without the bulk and inconvenience of traditional perfume storing containers. The second case provides the wearer with a continually available source of fragrance which does not need to be constantly recharged due to the evaporation of perfume during times when the fragrance is not desired.

While the above-described embodiments disclose an earring structure 100 as the preferred form of ornamental casing, it will be appreciated that the invention may be practiced with any ornamental casing adapted for wear as personal jewelry. For example a pendant, finger ring, necklace or hairpiece may be provided with means for retaining a perfumed material or perfume cartridge, and a means for varying the rate of escape of fragrance. The respective jewelry casing may be worn either directly on the wearer's body, or indirectly as by the use of a chain, belt or the like. Furthermore, the means for retaining perfumed material need not be a hidden compartment in the casing, such as compartment 108 discussed above. Instead, an exposed area on the casing may be provided with prongs or other suitable fasteners for receiving and holding a decorative perfume cartridge.

It should thus be apparent that these and other changes and modifications in the specifically described embodiments can be carried out without departing from the scope and spirit of the invention, which is intended to be limited only by the scope of the accompanying claims.

What is claimed is:

1. An earring comprising:
   an ornamental casing having means for attaching the earring to a wearer's earlobe, and retaining means for removably retaining a cartridge;
   a cartridge disposed in said retaining means and having a solid perfumed material encased therein, said cartridge having an adjustable opening for selectively exposing said perfumed material to the ambient, which is substantially impervious to the fragrance of said perfumed material when said opening is shut;
   said cartridge further including a one-piece base having a depression containing said solid perfumed material, said depression being capable of retaining said perfumed material in its molten state, and a top piece adjustably mounted on said base so as to cover said depression when placed in a closed position and to expose said perfumed material in said depression to the ambient when placed in an open position;

said base being cylindrically shaped, the interior of said cylinder defining a circular arrangement as seen in a plan view along the axis of the cylinder, formed by a C-shaped depression abutting a substantially pie-segment-shaped plateau; and said top piece comprising a circular disc rotatably mounted over said circular arrangement, have an eccentric aperture for exposing said perfumed material to the ambient when said aperture is rotated to a position overlying said depression.

2. An earring as in claim 1, wherein said plateau has a top surface disposed in a plane perpendicular to said cylindrical axis, and said circular disc is mounted flush with said top surface, said base further including an inner ridge disposed about the periphery of said C-shaped depression and co-planar with the top surface of said plateau, said plateau and ridge cooperatively providing continuous support to the periphery of said circular disc in any rotational position.

3. An earring as in claim 2, wherein said base has an axial cavity and said top piece has a centrally disposed tapered boss for mating with said axial cavity, at least one of said cavity and boss being tapered to provide a frictional fit between said top piece and base.

4. An earring as in claim 3, wherein said top piece further comprises a raised bar diametrically disposed on said circular disc for facilitating rotation of said top piece relative to said base.

5. A cartridge for holding and dispensing perfume, comprising:

a one-piece base having a depression containing a solid perfumed material, said depression being capable of retaining said perfumed material in its molten state;

a top piece adjustably mounted on said base so as to cover said depression when placed in a closed position and to expose said perfumed material in said depression to the ambient when placed in an open position;

said base being cylindrically shaped, the interior of said cylinder defining a circular arrangement, as seen in a plan view along the axis of the cylinder, formed by a C-shaped depression abutting a substantially pie-segment-shaped plateau; and said top piece comprising a circular disc rotatably mounted over said circular arrangement, having an eccentric aperture for exposing said perfumed material to the ambient when said aperture is rotated to a position overlying said depression.

6. A cartridge as in claim 5, wherein said plateau has a top surface disposed in a plane perpendicular to said cylindrical axis, and said circular disc is mounted flush with said top surface, said base further including an inner ridge disposed about the periphery of said C-shaped depression and co-planar with the top surface of said plateau, said plateau and ridge cooperatively providing continuous support to the periphery of said circular disc in any rotational position.

7. A cartridge as in claim 6, wherein said base has an axial cavity and said top piece has a centrally disposed tapered boss for mating with said axial cavity, at least one of said cavity and boss being tapered to provide a frictional fit between said top piece and base.

8. An earring as in claim 7, wherein said top piece further comprises a raised bar diametrically disposed on said circular disc for facilitating rotation of said top piece relative to said base.

* * * * *